United States Patent [19]
Niwa

[11] Patent Number: 4,501,147
[45] Date of Patent: Feb. 26, 1985

[54] CONTROL CIRCUIT FOR A HUMIDITY SENSOR

[75] Inventor: Takashi Niwa, Nara, Japan

[73] Assignee: Matsushita Electric Industrial Co., Ltd., Kadoma, Japan

[21] Appl. No.: 420,220

[22] PCT Filed: Jan. 13, 1982

[86] PCT No.: PCT/JP82/00010
§ 371 Date: Sep. 10, 1982
§ 102(e) Date: Sep. 10, 1982

[87] PCT Pub. No.: WO82/02598
PCT Pub. Date: Aug. 5, 1982

[30] Foreign Application Priority Data

Jan. 16, 1981 [JP] Japan .................. 56-5259

[51] Int. Cl.³ .................. G01W 1/00; H05B 6/68
[52] U.S. Cl. .................. 73/336.5; 73/73; 219/10.55 B
[58] Field of Search ............. 219/10.55 B, 10.55 R; 324/65 R; 73/336.5, 73, 75

[56] References Cited

U.S. PATENT DOCUMENTS 3,983,527  9/1976  Ohsato et al. .............. 73/336.5
4,080,564  4/1978  Nitta et al. .............. 219/10.55 B
4,261,179  9/1978  Dageford .............. 73/336.5
4,335,293  6/1980  Kobayashi et al. .............. 73/336.5
4,336,433  7/1980  Yokozeki et al. .............. 73/336.5
4,383,158  12/1980  Niwa .............. 219/10.55 B

FOREIGN PATENT DOCUMENTS 53-70497  6/1978  Japan .

Primary Examiner—Gerald Goldberg
Assistant Examiner—Hezron Williams
Attorney, Agent, or Firm—Wenderoth, Lind & Ponack

[57] ABSTRACT

A control circuit for controlling the self-cleaning function of a humidity sensor provides accurate control of the temperature of a humidity responsive region during the self-cleaning mode and an improved humidity detecting characteristic during the humidity detecting mode by changing the characteristics of the control circuit for the humidity sensor having self-cleaning function through the variation of resistances, such a variation being dependent upon the mode of the sensor.

5 Claims, 11 Drawing Figures

CONTROL CIRCUIT FOR A HUMIDITY SENSOR

BACKGROUND OF THE INVENTION

This invention relates to a control circuit for controlling the self-cleaning function of a humidity sensor, and its object is to switch the characteristics of a control circuit for a ceramic humidity sensor having a self-cleaning function through changes in a resistance value from the self-cleaning mode to the humidity detecting mode or vice versa so as to thereby ensure an accurate control of the temperature of its humidity responsive region in its self-cleaning mode and an improved humidity detecting performance in its humidity detecting mode.

With advances in the art of sensors and microcomputers, an automated cooking appliance has been put into practical use in which a humidity sensor is provided for sensing variations in the relative humidity in a heating chamber which are caused by the steam generated from the cooking food so as to thereby monitor the progress of cooking and then automatically detect the completion of the cooking or enabling the switching of an output level.

The humidity sensor, because of its very nature as a humidity detecting means, is constantly exposed to the smoke, steam, oil and so forth generated from the cooking food, with the consequence that the humidity responsive region of the sensor becomes fouled and unable to sense the humidity accurately after a long time of use. For a sensor whose humidity responsive region is made of ceramic material, that is, a so-called ceramic humidity sensor, a self-heating heater is installed on its humidity responsive surface and periodically energized to burn out such dirt and to restore its humidity responsive characteristics that is, a refresh operation of the sensor. A way to control such a heating temperature depends upon the thermistor property of the sensor.

SUMMARY OF THE INVENTION

Accordingly, it is an object of the present invention to provide a circuit arrangement which insures more accurate measurements of humidity and more accurate control of refresh temperatures by switching a humidity sensor control circuit when switching from its refresh operation mode to its humidity detection mode.

Specific embodiments of the present invention will now be described with reference to the accompanying drawings.

BRIEF DESCRIPTION OF THE DRAWINGS

FIG. 6(1) is a plot showing the output voltage v. resistance characteristic of the thermistor in the circuit as illustrated in FIG. 4;

FIG. 6(2) is a plot showing the relative humidity v. resistance characteristic of the humidity sensor;

DESCRIPTION OF THE PREFERRED EMBODIMENT

Referring to FIGS. 1 through 5, microwaves from a magnetron 1 are fed into the interior of an oven 3 by way of a waveguide 2 and then absorbed by the food to be cooked. An airflow generated by a cooling fan 4 used for cooling the magnetron 1, after cooling the magnetron 1, enters the interior of the oven 3 via a punched portion 5 of a wall of the oven 3 and exits a housing 8 via an opposite punched portion 6 and an air guide 7. A humidity sensor 9 which is disposed within the air guide 7 senses the relative humidity in the air outlet and in other words senses the relative humidity in the oven 3.

Figure 1:
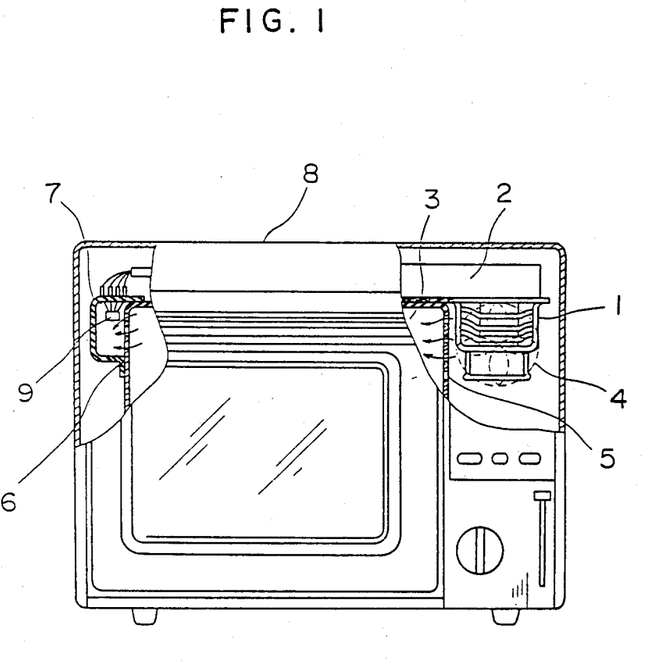
FIG. 1 is a fragmentally front view of a microwave oven to which a ceramic humidity sensor is incorporated.
Figure 2:
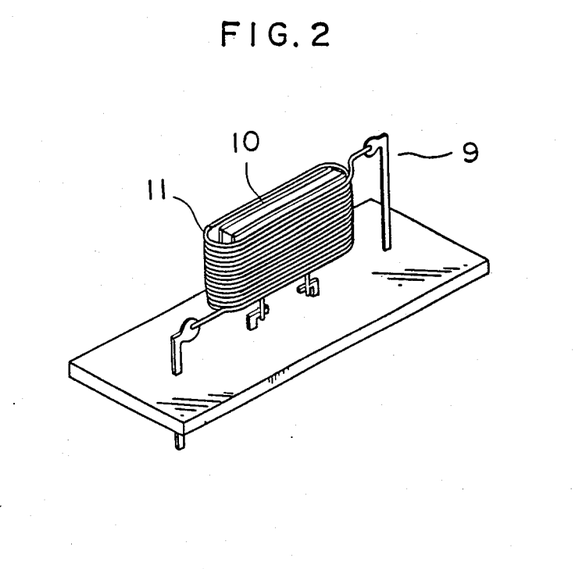
FIG. 2 is a perspective view showing the appearance of the ceramic humidity sensor as a principal component.
Figure 3:
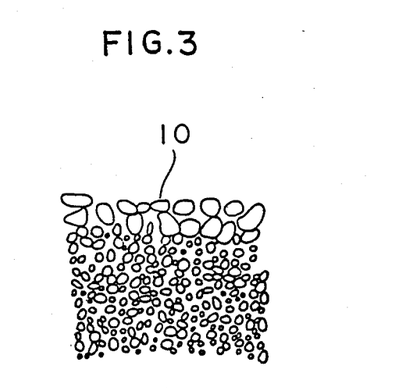
FIG. 3 is an enlarged cross sectional view of a humidity responsive region of the ceramic humidity sensor as shown in FIG. 1.

The humidity sensor 9, as shown in FIG. 2, has its humidity responsive region 10 made of a metal oxide ceramic (porous sintered material consisting of $MgCr_2O_4$ and $TiO_2$) having a multiplicity of fine apertures throughout its entirety and is designed to sense the relative humidity in the oven 3 (which is variable due to the steam generated from the food being heated) through the utilization of the phenomenon that the conductivity of the metal oxide ceramic varies as a function of humidity of the air within the fine apertures.

However, in the event that the humidity responsive region 10 becomes dirty with dust in the air, oil, smoke and so forth, the humidity responsive characteristics would be downgraded. An approach to overcome the problem has been suggested by which a heater 11 is installed so as to face against the humidity responsive region and is energized so as to burn out such dirt and recover its humidity responsive characteristics (that is, a refresh operation of the sensor). A way to control such a refresh temperature relies upon the use of a thermistor property (i.e.—the resistance decreases with a temperature rise as seen from FIG. 5). The characteristics of the ceramic humidity sensor, however, are such that its resistance varies drastically from $10^8\Omega$ to $10^4\Omega$ due to the properties of its starting material as shown in FIG. 6(2) when the relative humidity varies from 0% to 100%. To make the most of the sensor whose resistance varies drastically in the above manner, the characteristic of an amplifier necessary for converting the resistance change into a voltage of a given amplitude should be selected such that it shows a higher gain for an input signal of a small amplitude and a lower gain for that of a greater amplitude and shows a smooth variation in its output voltage for $10^4$ variations in the resistance of the sensor. As indicated by the solid line in FIG. 6(1), the resistance v. output voltage characteristic curve has a very gentle gradient about a refresh detection resistance of 5 K$\Omega$. In attempting to decide from the output voltage whether the humidity responsive region 10 of the humidity sensor 9 has reached the refresh temperature, the refresh temperature varies greatly due to deviations in circuit constants and voltage levels so that the refresh operation may excessively increase the temperature and destroy the sensor or insufficiently increase the temperature to an extent which does not assure satisfactory cleaning but rather allows the deterioration in the humidity responsive characteristics of the sensor.

Therefore, the object of the present invention is to provide a circuit arrangement which insures a more stable refresh operation of the sensor by modifying the resistance v. output voltage characteristics during the refresh operation mode (the phantom line) with respect to that present during the humidity detection mode (the dotted line) as shown in FIG. 6(1). The characteristics are modified with the aid of dividing resistors connected to an input stage of the amplifier. Details of the present invention will now be discussed with reference to FIGS. 4 through 8.

Figure 4:
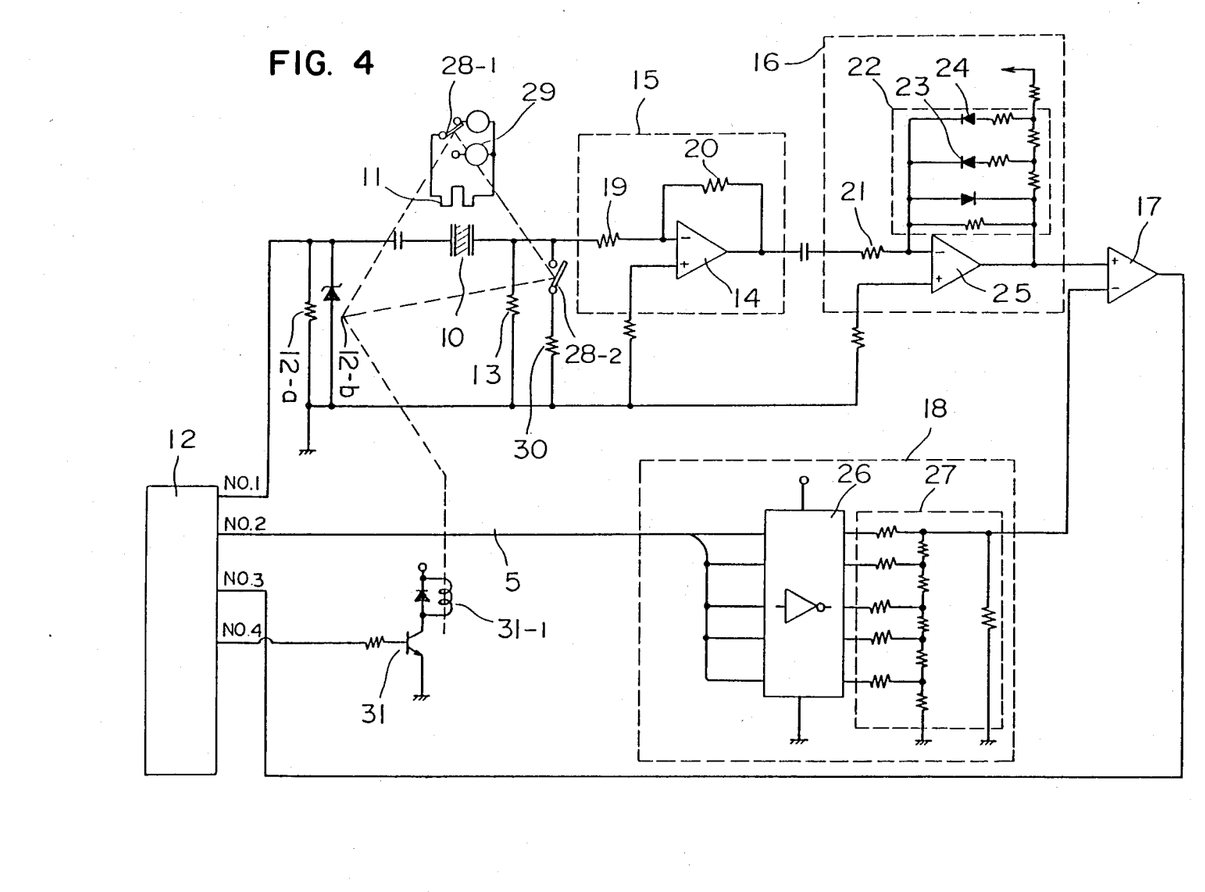
FIG. 4 is a circuit diagram of a humidity sensor control circuit.

In FIG. 4, the voltage which is supplied to operational amplifier 14 is the voltage which appears across resistor 13 i.e.; the voltage stabilized by resistor 12a at zener diode 12b minus the voltage drop across the humidity responsive region 10. After being amplified by two cascaded inverter amplifiers 15 and 16, the input voltage is supplied to a + input of a comparator 17 and compared with a − input voltage from a reference voltage generator 18. The output of the comparator 17 is fed to terminal No. 3 of the microcomputer 12 so that the output voltage of the sensor circuit may be converted into a digital value. The gain of the first stage inverter amplifier 15 is determined by the resistance ratio of a resistor 19 to a resistor 20, while that of the next succeeding stage inverter amplifier 16 is determined by a ratio of the resistance of a resistor 21 to the combined resistance of a group of resistors 22. Diodes 23 and 24 are turned on and off so as to vary the combined resistance of the group of feedback resistors connected to an operational amplifier 25, the diodes be turned on and off depending upon the amplitude of the output voltage from the operational amplifier 25, so that the output voltage shows a gentle gradient for a $10^4$ variation in the resistance of the sensor. The humidity detecting property of this circuit arrangement is depicted by the dotted line in FIG. 6(1). The reference voltage generator 18 includes a C-MOS IC 26 and a ladder circuit 27 and is designed to convert 5 bit outputs from terminal No. 2 (consisting of five lines) of the microcomputer 12 into the corresponding one of 32 (i.e., $2^5$) analog voltages.

During the detection of the end of a refresh operation, a relay contact 28-1 is placed into a high voltage circuit side 29 so as to heat the self-heating heater 11. Another relay contact 28-2 is also switched on so as to place a dividing resistor 30 in parallel with resistor 13 during the refresh operation. The property of the circuit arrangement at this time is depicted by the phantom line in FIG. 6(1).

Although in the above illustrated embodiment the gradient of the resistance v. output voltage characteristic curve of the circuit arrangement during the humidity detection mode is made substantially equal to that during detection of the temperature of the humidity responsive region being heated by the heater, the present invention should not be limited thereto and all that is necessary for the present invention is to vary the circuit characteristics in order to insure accurate detection and stable refresh operation.

The relay contacts 28-1 and 28-2 are activated by turning on a transistor 31 and energizing a relay coil 31-1 in response to the output of terminal No. 4 of the microcomputer 12.

Figure 5:
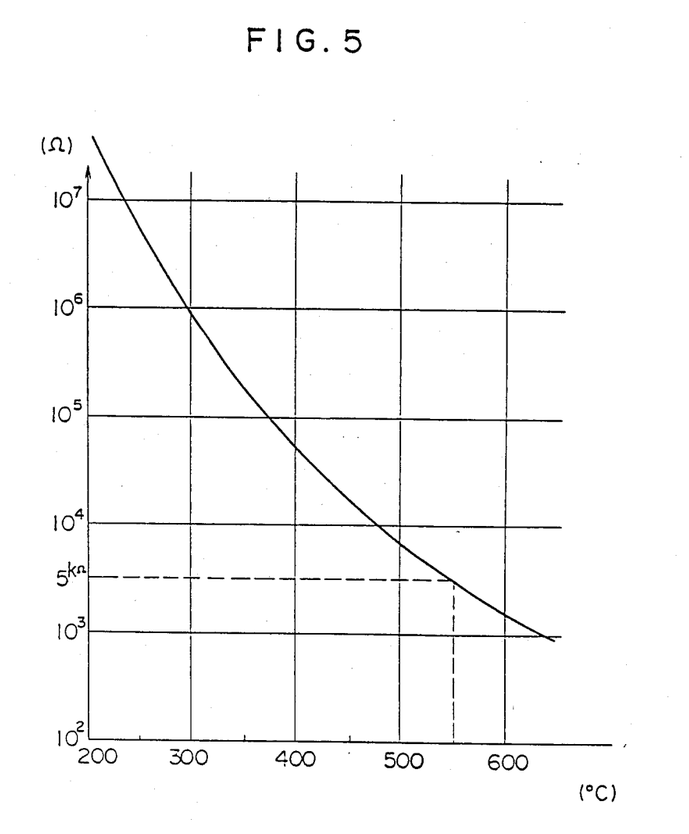
FIG. 5 is a thermistor characteristic of the humidity sensor.
Figure 6:
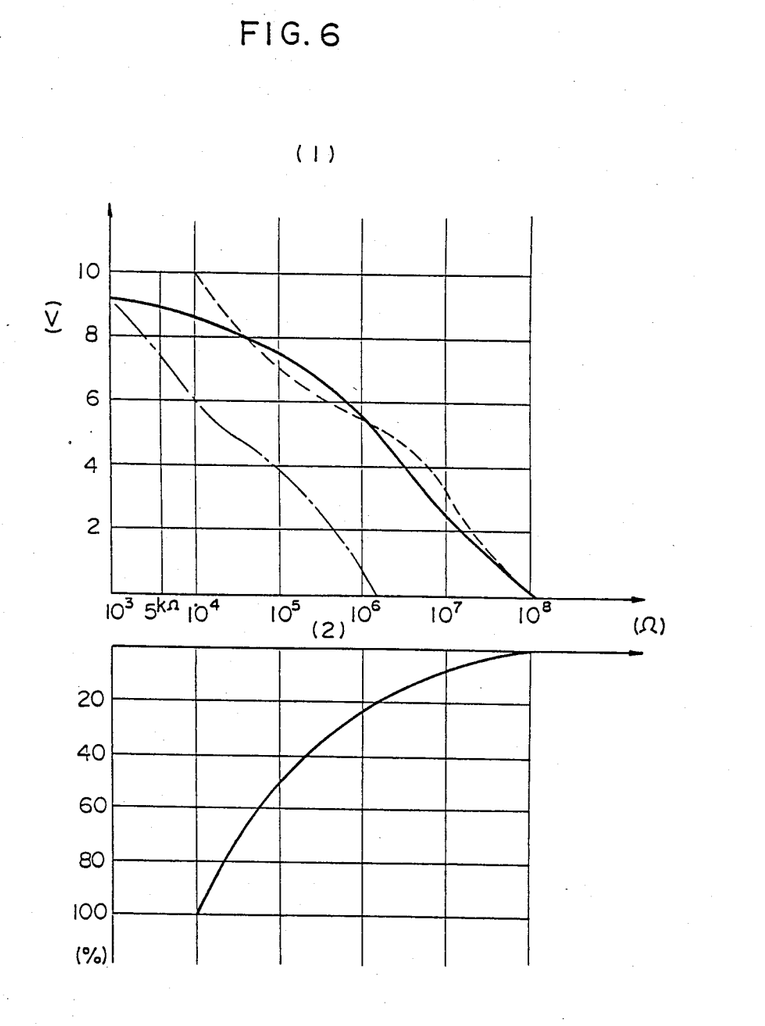
Figure 7:
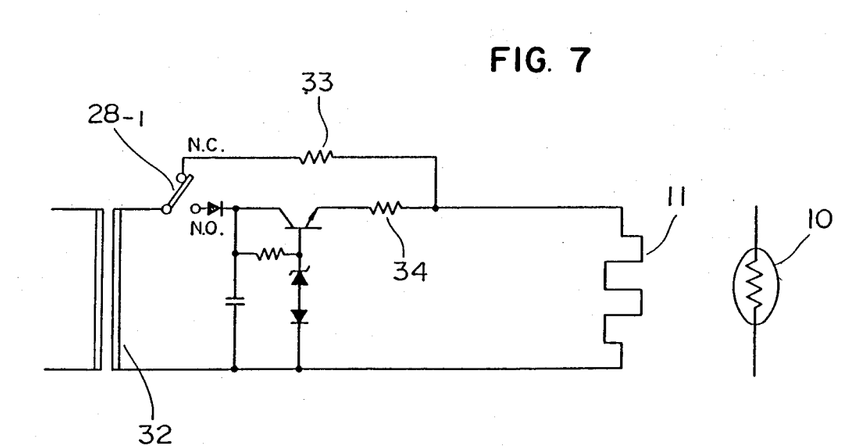
FIG. 7 is a circuit diagram of a power supply circuit for a heater as shown in FIG. 4.

As is clear from FIG. 7, the self-heating heater 11 is supplied with the output voltage from the secondary 32 of a low voltage transformer which is divided between a resistor 33 and the self-heating heater 11, when the relay contact 28-1 is on its N.C. side. This prevents the humidity responsive region from becoming wet with dew and deteriorating its humidity response. On the other hand, when the relay contact 28-1 is on its N.O. side, the output voltage of the secondary 32 of the low voltage transformer is DC-stabilized and divided through a resistor 34 and the self-heating heater 11 and is supplied to the self-heating heater 11 so as to thereby heat the humidity responsive region 10. The temperature dependency of the resistance of the sensor is shown in FIG. 5.

Figure 8:
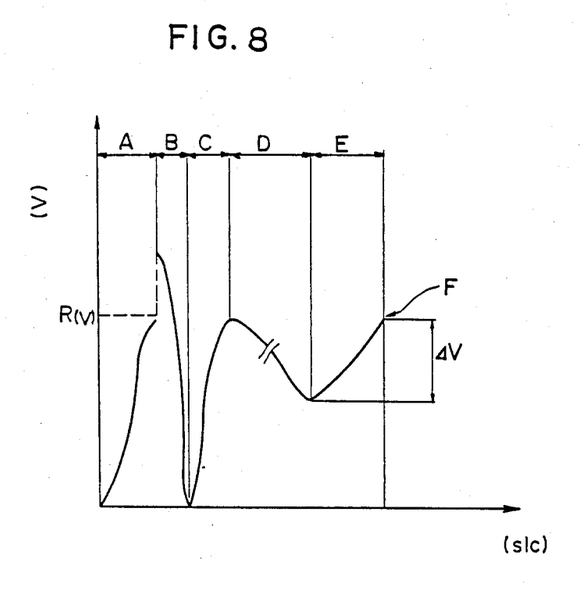
FIG. 8 is a diagrammatic view of time-wise variations of an input to the comparator as shown in FIG. 4.

FIG. 8 is a view showing the relationship between the food cooking time and the voltage at the + input terminal of the comparator 17, wherein the circuit arrangement manifests the refresh characteristic (as depicted by the phantom line in FIG. 6(1) during time slot A. In addition, when the refresh level reaches R(V), the circuit arrangement shows the humidity detecting characteristic (the dotted line in FIG. 6(1) because the relay contact 28-1 is in its open position or the N.C. side. During time slot B, the humidity sensor 9 recovers its humidity characteristic where the humidity is low due to a high temperature in the humidity responsive region 10 and the input to the comparator shows a sharp decline. Since the humidity sensor 9 is gradually cooled with the air from the cooling fan 4 during time slot C, the comparator input increases up to a value corresponding to the relative humidity in the atmosphere. Provided that heating goes on under these circumstances, the internal temperature of the oven 3 rises but the food has not yet generated steam so that the relative humidity in the oven 3 drops and the comparator input voltage corresponding to the relative humidity in the atmosphere therefore declines (time slot D). On the other hand, if the food starts generating steam, then the input voltage rises suddenly (time slot E). The humidity is monitored at the moment where the input increases from its minimum by $\Delta V$ (time slot F).

Figure 9:
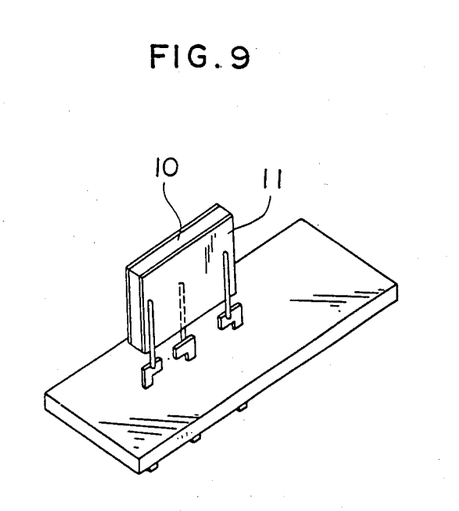
FIG. 9 is a perspective view of a ceramic humidity sensor having a heater disposed over its humidity responsive region.

FIG. 9 illustrates an example of the above described humidity sensor 9 having the self-heating heater 11 disposed on a surface of the humidity responsive region 10 by painting.

Figure 10:
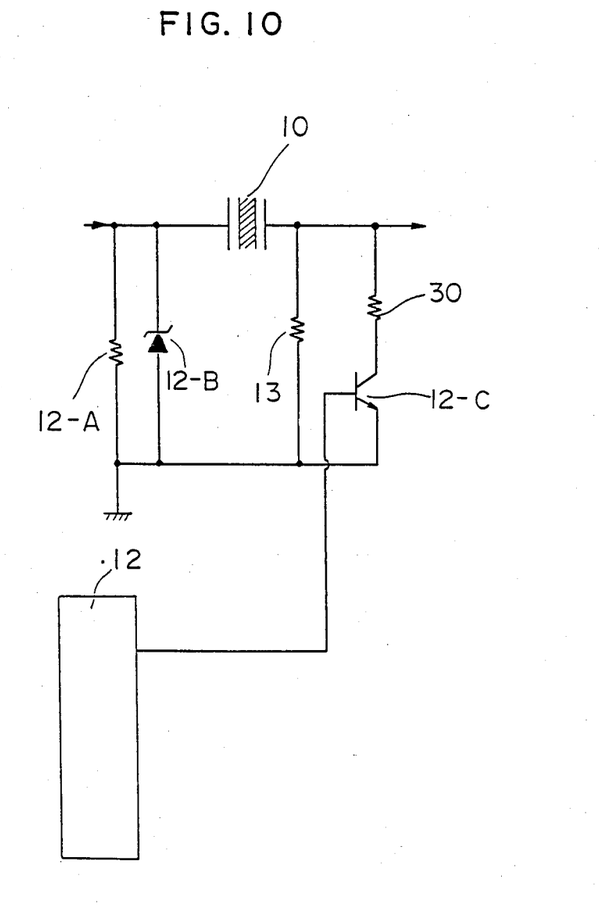
FIG. 10 is a circuit diagram of a humidity sensor control circuit.

In FIG. 10, another embodiment of the present invention is illustrated wherein the dividing resistors are switched by a transistor and especially this transistor is switched on to place the resistor 30 in parallel with the resistor 13 in response to an output from the microcomputer 12.

As described hereinbefore, more accurate refresh detection operation is ensured even with differences in the circuit constants, by varying the value of the dividing resistors in the circuit arrangement of FIG. 4 and modifying the characteristics of the circuit arrangement during the refresh mode with respect to that present during the humidity detection mode, then when no difference in the characteristics are present between both operation modes. There is no fear of thermally destroying the sensor or deteriorating the humidity detection characteristics due to insufficient refreshing. Furthermore, it is possible to use a wider range of the amplitude of the output voltage for variations in the relative humidity as seen from FIGS. 6(1) and 6(2) due to the distinguished refresh characteristics and to attain a higher resolution at high humidities than under other saturations. These provide advantageous features for the benefit of automatic cooking.

I claim:

1. In a circuit arrangement comprising a humidity sensor with a humidity responsive region and a heater for heating said humidity responsive region, a power supply circuit for supplying power to said heater, a means for switching on and off the power supplied from said power supply circuit to said heater, a resistor connected in series with said humidity responsive region of said humidity sensor, a means for supplying a voltage across said humidity responsive region and said resistor, and an amplifier circuit for amplifying a voltage which appears across said resistor, a control circuit for said humidity sensor having a means to change the resistance value of said resistor such that a curve of said amplifier circuit's output voltage vs. the resistance of said humidity sensor's humidity responsive region characteristic present during humidity detection is different from that present during detection of the temperature of said humidity responsive region being heated by said heater.

2. A control circuit for a humidity sensor as set forth in claim 1, wherein the gradient of a said output voltage vs. resistance characteristic curve during humidity detection is made substantially equal to that present during detection of the temperature of said humidity responsive region being heated by said heater.

3. A control circuit for a humidity sensor as set forth in claim 1, wherein another resistor is connected in parallel with said resistor through a relay contact switch as a means of changing the resistance value connected in series with said humidity responsive region of said humidity sensor.

4. A control circuit for a humidity sensor as set forth in claim 1, wherein a semiconductor elements is used as means for varying the resistance value of said resistor.

5. A control circuit for a humidity sensor as set forth in claim 1, wherein two relay contact switches are energized by a common excitation coil as a means of changing the resistance value of said resistor and a means for switching on and off the power supply circuit to said heater.

* * * * *